United States Patent
Gross et al.

(10) Patent No.: US 7,473,280 B2
(45) Date of Patent: Jan. 6, 2009

(54) COLORING AGENT COMPOSITIONS AND METHODS OF TREATING KERATIN FIBERS THEREWITH

(75) Inventors: Wibke Gross, Düsseldorf (DE); Sandra Mausberg, Erkrath (DE); Doris Oberkobusch, Düsseldorf (DE); Horst Höffkes, Düsseldorf (DE)

(73) Assignee: Henkel KGaA, Dusseldorf (DE)

( * ) Notice: Subject to any disclaimer, the term of this patent is extended or adjusted under 35 U.S.C. 154(b) by 0 days.

(21) Appl. No.: 11/664,808

(22) PCT Filed: Sep. 29, 2005

(86) PCT No.: PCT/EP2005/010515

§ 371 (c)(1),
(2), (4) Date: Nov. 8, 2007

(87) PCT Pub. No.: WO2006/040015

PCT Pub. Date: Apr. 20, 2006

(65) Prior Publication Data

US 2008/0189877 A1 Aug. 14, 2008

(30) Foreign Application Priority Data

Oct. 8, 2004 (DE) ........................ 10 2004 049 363

(51) Int. Cl.
*A61Q 5/10* (2006.01)
*C07D 249/00* (2006.01)

(52) U.S. Cl. ............... 8/405; 8/406; 8/407; 8/408; 8/409; 8/565; 8/567; 8/570; 548/262.4

(58) Field of Classification Search ............... 8/405, 8/406, 408, 409, 565, 567, 570; 548/262.4
See application file for complete search history.

(56) References Cited

U.S. PATENT DOCUMENTS

| | | |
|---|---|---|
| 4,865,774 A | 9/1989 | Fabry et al. |
| 4,931,218 A | 6/1990 | Schenker et al. |
| 5,061,289 A | 10/1991 | Clausen et al. |
| 5,294,726 A | 3/1994 | Behler et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 6,099,592 A | 8/2000 | Vidal et al. |
| 6,284,003 B1 | 9/2001 | Rose et al. |
| 7,306,631 B2 * | 12/2007 | Glenn et al. ............... 8/405 |
| 2005/0144740 A1 | 7/2005 | Gross et al. |

FOREIGN PATENT DOCUMENTS

| | | |
|---|---|---|
| DE | 23 59 999 | 6/1975 |
| DE | 37 23 354 | 1/1989 |
| DE | 37 25 030 | 2/1989 |
| DE | 38 43 892 | 6/1990 |
| DE | 39 26 344 | 2/1991 |
| DE | 41 33 957 | 4/1993 |
| DE | 195 43 988 | 5/1997 |
| DE | 102 41 076 | 3/2004 |
| EP | 0 740 931 | 8/1997 |
| EP | 0 998 908 | 5/2000 |
| EP | 1 433 468 | 6/2004 |
| GB | 1026978 | 4/1966 |
| GB | 1153196 | 5/1969 |
| JP | 02/019576 | 1/1990 |
| WO | WO-94/08969 | 4/1994 |
| WO | WO-94/08970 | 4/1994 |
| WO | WO-96/15765 | 5/1996 |

OTHER PUBLICATIONS

STIC Search Report dated Aug. 14, 2008.*
H. Möhrle et al., "Zum Identitätsnachweis von Coffein im Arzneibuch; 1. Mitt: Imidazo[1,5-a]pyrimidiniumsalze", Pharmazie, 1999, vol. 54, No. 2, pp. 115-123.
H. Möhrle et al., "Zum Identitätsnachweis von Coffein im Arzneibuch; 2. Mitt: Struktur des Farbstoffs aus Modifizierter Reaktion", Pharmazie, 1999, vol. 54, No. 4, pp. 269-279.
C. Zviak (Ed.), "The Science of Hair Care", pp. 248-250 & 264-267, Marcel Dekker, Inc., New York, NY, 1986.

* cited by examiner

*Primary Examiner*—Eisa B Elhilo
(74) *Attorney, Agent, or Firm*—Connolly Bove Lodge & Hutz LLP

(57) ABSTRACT

Fiber-coloring components for dye compositions and methods for using the same, wherein the compositions comprise: (i) at least one component A comprising a compound selected from imidazo[1,5-a]pyrimidinium derivatives of general formula I, enamine counterparts of such derivatives, and mixtures thereof:

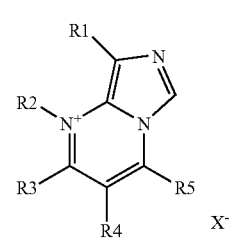

(I)

and (ii) at least one component B comprising a reactive carbonyl compound.

20 Claims, No Drawings

COLORING AGENT COMPOSITIONS AND METHODS OF TREATING KERATIN FIBERS THEREWITH

CROSS-REFERENCE TO RELATED APPLICATIONS

This application is a national stage application, under 35 U.S.C. §371, of PCT/EP2005/010515, filed Sep. 29, 2005, which claims priority of German Application No. 10 2004 049 363.4, filed Oct. 8, 2004.

BACKGROUND OF THE INVENTION

The invention relates to an agent for coloring fibers containing keratin, in particular human hair, said agent comprising cationic imidazo[1,5-a]pyrimidinium derivatives in combination with reactive carbonyl compounds, the use of this combination in agents for coloring fibers containing keratin, for refreshing the color or nuancing previously colored fibers containing keratin as well as a method for coloring fibers containing keratin, in particular human hair.

Generally, either substantive dyes or oxidation dyes that result from oxidative coupling of one or more developer components with each other or with one or more coupler components are used for coloring fibers containing keratin. Coupler components and developer components are also called oxidation dye precursors.

Normally, primary aromatic amines with an additional free or substituted hydroxyl or amino group in the para or ortho position, diaminopyridine derivatives, heterocyclic hydrazones, 4-aminopyrazole derivatives as well as 2,4,5,6-tetraaminopyrimidine and derivatives thereof are employed as the developer components.

Specific exemplary representatives are p-phenylenediamine, p-toluylenediamine, 2,4,5,6-tetraaminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazolone-5,4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

m-Phenylenediamine derivatives, naphthols, resorcinol and resorcinol derivatives, pyrazolones, m-aminophenols and substituted pyridine derivatives are generally used as the coupling components. Particularly suitable coupling substances are α-naphthol, 1,5-dihydroxynaphthalene, 2,7-dihydroxynaphthalene and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)anisole (Lehmann's Blue), 1-phenyl-3-methylpyrazolone-5,2,4-dichloro-3-aminophenol, 1,3-bis(2',4'-diaminophenoxy) propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine.

In regard to further typical dye components, reference is expressly made to the series "Dermatology", edited by Ch. Culnan and H. Maibach), Verlag Marcel Dekker Inc., New York, Basel, 1986, volume 7, Ch. Zviak, The Science of Hair Care, chapter 7, (pages 248-250 (substantive dyes), and chapter 8, pages 264-267 (oxidation dyes), as well as the "European Inventory of Cosmetic Raw Materials", published by the European Union, obtainable in disk form from the Bundesverband Deutscher Industrie-und Handelsunternehmen fur Arzneimittel, Reformwaren und Körperpflegemittel e.V., Mannheim.

Indeed, with the oxidation dyes, intensive colorations can be achieved with good fastness characteristics, but the development of the color normally occurs in the presence of oxidizing agents such as e.g. $H_2O_2$, which in some cases can result in damage to the fibers. It still proves problematic to prepare oxidative hair colorations in the red tones having adequate fastness characteristics, especially with very good wash fastness and rubbing fastness.

Furthermore, some oxidation dye precursors or certain mixtures of oxidation dye precursors sometimes have a sensitizing effect on people with delicate skin. Substantive dyes are applied under more gentle conditions, but their disadvantage is that the colorations often possess only inadequate fastness characteristics.

Dyes, comprising CH-acidic, cationic imidazo[1,5-a]pyrimidinium derivatives corresponding to Formula I in combination with reactive carbonyl compounds, as well as the use of this combination for dyeing fibers containing keratin or for color refreshing or nuancing already dyed fibers containing keratin, are unknown up to now.

BRIEF SUMMARY OF THE INVENTION

The object of the present invention is to provide dyes for fibers containing keratin, especially human hair, which in regard to the color depth and fastness characteristics, such as for example light fastness, rubbing fastness and wash fastness as well as fastness to perspiration and cold waving, are qualitatively at least equivalent to the conventional oxidation hair dyes, without, however being necessarily dependent on oxidizing agents such as e.g. $H_2O_2$. Furthermore, the dyes must have no or only a very slight sensitization potential.

Surprisingly, it has now been found that the compounds illustrated in Formula I in combination with compounds comprising at least one reactive carbonyl group are eminently suitable, even in the absence of oxidizing agents, for dyeing fibers containing keratin. They produce colorations with excellent brilliance and depth of color and lead to a wide range of color nuances. In particular, colorations are obtained with improved fastness characteristics over a range of nuances from yellow through orange, brown orange, brown, red, red-violet up to blue-violet and dark blue. However, in principle the use of oxidizing agents should not be excluded.

A first subject matter of the invention is an agent for coloring fibers containing keratin, especially human hair, comprising at least one compound corresponding to Formula I and/or its enamine form as the component A in a cosmetic carrier,

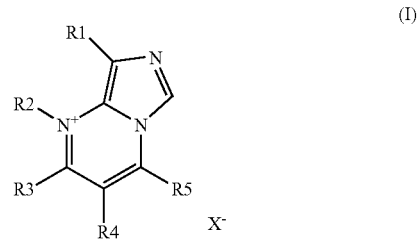

(I)

wherein
$R^1$ stands for a hydrogen atom, a halogen atom, carboxyl group, a ($C_1$-$C_6$) alkoxy group, ($C_1$-$C_6$) alkyl group, a ($C_2$-$C_6$) alkenyl group, an optionally substituted aryl group, an aryl ($C_1$-$C_6$) alkyl group, a ($C_2$-$C_6$) hydroxyalkyl group, a ($C_2$-$C_6$) polyhydroxyalkyl group or a $R^I R^{II} N$—CO— group, wherein $R^I$ and $R^{II}$ stand independently of one another for a hydrogen atom, a ($C_1$-$C_6$) alkyl group, a ($C_1$-$C_6$) alkenyl group, an aryl group or an aryl $C_1$-$C_6$ alkyl group, wherein $R^I$ and $R^{II}$ together with the nitrogen atom can form a 5-, 6- or 7 membered ring, and $R^2$ stands for a ($C_1$-$C_6$) alkyl group, a ($C_2$-$C_6$) alkenyl group, an optionally substituted aryl group, an aryl ($C_1$-$C_6$) alkyl group, a ($C_1$-$C_6$) hydroxyalkyl group, a ($C_2$-$C_6$) polyhydroxyalkyl group or a $R^{III} R^{IV} N$—$(CH_2)_n$— group, wherein $R^{III}$ and $R^{IV}$ stand independently of one another for a hydrogen atom, a ($C_1$-$C_6$) alkyl group, a ($C_1$-$C_6$) alkenyl group or an aryl $C_1$-$C_6$ alkyl group, wherein $R^{III}$ and $R^{IV}$ together with the nitrogen atom can form a 5-, 6- or 7 membered ring and n stands for a number 2, 3, 4, 5 or 6, at least one $R^3$ or $R^5$ group stands for a methyl group and the other group stands for a hydrogen atom, a ($C_1$-$C_6$) alkyl group, a ($C_2$-$C_6$) alkenyl group, an aryl group, an aryl ($C_1$-$C_6$) alkyl group, a ($C_2$-$C_6$) hydroxyalkyl group or a ($C_2$-$C_6$) polyhydroxyalkyl group, $R^4$ stands for a hydrogen atom, a ($C_1$-$C_6$) alkyl group, a ($C_2$-$C_6$) alkenyl group, a ($C_1$-$C_6$) hydroxyalkyl group, a ($C_2$-$C_6$) polyhydroxyalkyl group or an optionally substituted aryl group, $X^-$ means a physiologically compatible anion and as component B at least one reactive carbonyl compound.

DETAILED DESCRIPTION OF THE INVENTION

Keratin-containing fibers are understood to mean wool, furs, feathers and particularly human hair. However, the inventive dyes can, in principle, also be used for dyeing other natural fibers, such as e.g. cotton, jute, sisal, linen or silk, modified natural fibers, such as e.g. cellulose regenerate, nitrocellulose, alkyl cellulose or hydroxyalkyl cellulose or acetyl cellulose.

Examples of $C_1$-$C_6$ alkyl groups are the methyl, ethyl, propyl, isopropyl, n-butyl, sec-butyl and tert.-butyl, n-pentyl and n-hexyl groups. Propyl, ethyl and methyl are preferred alkyl groups. Examples of suitable cyclic alkyl groups are cyclopentyl and cyclohexyl.

Examples of preferred $C_2$-$C_6$ alkenyl groups are vinyl and allyl.

Preferred aryl groups are phenyl, naphthyl and biphenyl.

Preferred aryl ($C_1$-$C_6$) alkyl groups are benzyl and 2-phenylethyl.

Furthermore, preferred examples of a $C_1$-$C_6$ hydroxyalkyl group can be a hydroxymethyl, a 2-hydroxyethyl, a 2-hydroxypropyl, a 3-hydroxypropyl, a 4-hydroxybutyl group, a 5-hydroxypentyl and a 6-hydroxyethyl group. A 2-hydroxyethyl group is particularly preferred.

Examples of a $C_2$-$C_6$ polyhydroxyalkyl group are the 2,3-dihydroxypropyl group, 3,4-dihydroxybutyl group and the 2,4-dihydroxybutyl group.

It is inventively preferred when the $R^1$ group stands for a carbamoyl group $R^I R^{II} N$—CO—, wherein $R^I$ and $R^{II}$ independently of one another mean a hydrogen atom or a ($C_1$-$C_6$) alkyl group, particularly a methyl group.

It is inventively preferred when the $R^2$, $R^3$ and $R^5$ groups mean a methyl group in Formula (I).

It is inventively preferred when $R^4$ stands for a hydrogen atom or a ($C_1$-$C_6$) alkyl group.

It is preferred when $X^-$ in Formula (I) and the following Formula (II) is selected from halide (chloride, bromide, iodide), benzenesulfonate, p-toluenesulfonate, ($C_1$- to $C_4$) alkanesulfonate, trifluoromethanesulfonate, acetate, trifluoroacetate, perchlorate, 0.5 sulfate, hydrogen sulfate, tetrafluoroborate, hexafluorophosphate, hexafluorozincate, or tetrachlorozincate. Particularly preferably, $X^-$ stands for chloride, bromide, tetrafluoroborate or hydrogen sulfate.

Preferably, the compound corresponding to Formula I is selected from the group consisting of salts with physiologically compatible anions $X^-$ of 1,2,4-trimethyl-8-[(methylamino)carbonyl]imidazo[1,5-a]pyrimidinium (see Formula II), of 1,2,3,4-tetramethyl-8-[(methylamino)carbonyl]imidazo[1,5-a]pyrimidinium, of 3-ethyl-1,2,4-trimethyl-8-[(methylamino)carbonyl]imidazo[1,5-a]pyrimidinium, as well as of the enamine forms of the abovementioned salts. The numbering used for the atoms of the imidazo[1,5-a]pyrimidinium ring structure for naming the inventive compounds is illustrated in Formula II.

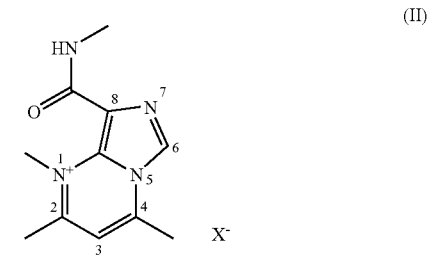

(II)

In general, those compounds that possess a hydrogen atom bonded to an aliphatic carbon atom, wherein the carbon-hydrogen bond is activated due to electron-withdrawing substituents, are recognized as CH-acidic compounds. The compounds corresponding to Formula I are CH-acidic compounds. The enamine form can be selectively prepared in the presence of a base. As an example of compounds corresponding to Formula (I), the enamine form is then illustrated as the compound of Formula (II) by the following Formulas (IIa) and (IIb).

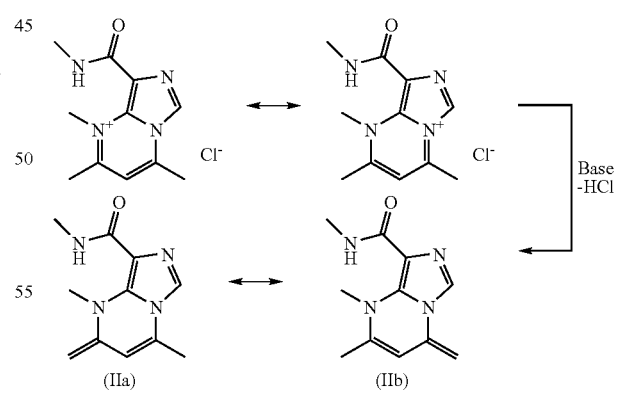

The CH-acidic compounds corresponding to Formula I are generally known in the literature. The inventive compounds corresponding to Formula (I) can be prepared by known synthetic methods in accordance with H. Möhrle et al., *Pharmazie*, 1999, 54(2), 115-123.

In the context of the invention, reactive carbonyl compounds as the component B possess at least one carbonyl group as the reactive group, which reacts with the CH-acidic compound according to Formula I to form a carbon-carbon bond. Preferred reactive carbonyl compounds are aldehydes and ketones, particularly aromatic aldehydes. Moreover, according to the invention, such compounds in which the reactive carbonyl group is protected or derivatized in such a manner that the carbon atom of the derivatized carbonyl group is still reactive towards the inventive CH-acidic compounds of Formula I can also be used as the component B. These derivatives are preferably addition compounds

- of amines and their derivatives, forming imines or oximes as the addition compounds
- of alcohols, forming acetals or ketals as the addition compounds
- of water, forming hydrates as the addition product (in this case c), component B is derived from an aldehyde)

on the carbon atom of the carbonyl group of the reactive carbonyl compound.

Preferred reactive carbonyl compounds of component B are selected from the group consisting of benzaldehyde and its derivatives, naphthaldehyde and its derivatives, cinnamaldehyde and its derivatives, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazol-3-aldehyde, 2-formylmethylene-1,3,3-trimethylindoline (Fischer's aldehyde or tribasic aldehyde), 2-indole aldehyde, 3-indole aldehyde, 1-methylindol-3-aldehyde, 2-methylindol-3-aldehyde, 2-(1',3',3'-trimethyl-2-indolinylidene)acetaldehyde, 1-methylpyrrole-2-aldehyde, 4-pyridine aldehyde, 2-pyridine aldehyde, 3-pyridine aldehyde, pyridoxal, antipyrin-4-aldehyde, furfural, 5-nitrofurfural, 2-thenoyl-trifluoroacetone, chromone-3-aldehyde, 3-(5'-nitro-2'-furyl)acrolein, 3-(2'-furyl)acrolein and imidazol-2-aldehyde, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, 9-methyl-3-carbazole aldehyde, 9-ethyl-3-carbazole aldehyde, 3-acetylcarbazole, 3,6-diacetyl-9-ethylcarbazole, 3-acetyl-9-methylcarbazole, 1,4-dimethyl-3-carbazole aldehyde, 1,4,9-trimethyl-3-carbazole aldehyde, 6-nitropiperonal, 2-nitropiperonal, 5-nitrovanillin, 2,5-dinitrosalicyl aldehyde, 5-bromo-3-nitrosalicyl aldehyde, 3-nitro-4-formylbenzenesulfonic acid, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 5-formyl-1-methylquinolinium-, 6-formyl-1-methylquinolinium-, 7-formyl-1-methylquinolinium-, 8-formyl-1-methylquinolinium-, 5-formyl-1-ethylquinolinium-, 6-formyl-1-ethylquinolinium-, 7-formyl-1-ethylquinolinium-, 8-formyl-1-ethylquinolinium, 5-formyl-1-benzylquinolinium-, 6-formyl-1-benzylquinolinium-, 7-formyl-1-benzylquinolinium-, 8-formyl-1-benzylquinolinium-, 5-formyl-1-allylquinolinium-, 6-formyl-1-allylquinolinium-, 7-formyl-1-allylquinolinium- and 8-formyl-1-allylquinolinium benzenesulfonate, -p-toluenesulfonate, -methanesulfonate, -perchlorate, -sulfate, -chloride, -bromide, -iodide, -tetrachlorozincate, -methylsulfate-, -trifluoromethanesulfonate, -tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, as well as any mixture of the above compounds.

Benzaldehyde, cinnamaldehyde and naphthaldehyde together with their derivatives, in particular with one or more hydroxyl, alkoxy or amino substituents, are quite particularly preferred as the reactive carbonyl compounds in the inventive agents. Again, the compounds according to Formula (Ca-1) are preferred.

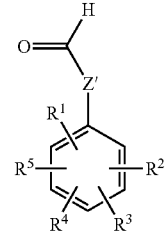

(Ca-1)

wherein $R^1$, $R^2$ and $R^3$ independently of each other stand for a hydrogen atom, a halogen atom, a $C_1$-$C_6$ alkyl group, a hydroxyl group, a $C_1$-$C_6$ alkoxy group, a $C_1$-$C_6$ dialkylamino group, a di($C_2$-$C_6$ hydroxyalkyl)amino group, a di($C_1$-$C_6$ alkoxy $C_1$-$C_6$ alkyl)amino group, a $C_1$-$C_6$ hydroxyalkyloxy group, a sulfonyl group, a carboxyl group, a sulfonic acid group, a sulfonamido group, a sulfonamide group, a carbamoyl group, a $C_2$-$C_6$ acyl group, an acetyl group or a nitro group, Z' stands for a direct bond or a vinylene group, $R^4$ and $R^5$ stand for a hydrogen atom or together form a 5- or 6-membered aromatic or aliphatic ring with the rest of the molecule.

The derivatives of benzaldehyde, naphthaldehyde or cinnamaldehyde of the reactive carbonyl compound according to component B are particularly preferably selected from 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitro-salicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-(1-Imidazolyl)benzaldehyde and piperonal. Together, these representatives are the particularly preferred additional reactive carbonyl compounds of the component B.

In a second embodiment, it can be advantageous for broadening the color spectrum to add at least one further compound as the component C in addition to at least one compound corresponding to Formula (I) as the component A and at least one compound of the component B. The compound of component C is preferably selected from CH-acidic compounds that are different from compounds of Formula (I).

The additional CH-acidic compounds of component C are preferably selected from the group consisting of salts formed from 1,4-dimethylquinolinium, 1-ethyl-4-methylquinolinium, 1-ethyl-2-methylquinolinium, 1,2,3,3-tetramethyl-3H-indolium, 2,3-dimethyl-benzothiazolium, 2,3-dimethyl-naphtho[1,2-d]thiazolium, 3-ethyl-2-methyl-naphtho[1,2-d]thiazolium, 3-ethyl-2-methyl-benzoxazolium, 1,2,3-trimethylquinoxalinium, 3-ethyl-2-methyl-benzothiazolium, 1,2-dihydro-1,3,4,6-tetramethyl-2-oxo-pyrimidinium, 1,2-dihydro-1,3,4-trimethyl-2-oxo-pyrimidinium, 1,2-dihydro-4,6-dimethyl-1,3-dipropyl-2-oxo-pyrimidinium, 1,2-dihydro-1,3,4,6-tetramethyl-2-thioxo-pyrimidinium, 1,2-dihydro-1,3,4,5,6-pentamethyl-2-oxo-pyrimidinium, 2,5-dimethyl-3-(2-propenyl)-1,3,4-thiadiazolium, 3-ethyl-2,5-dimethyl-1,3,4-thiadiazolium, 1,2-dimethylquinolinium and 1,3,3-trimethyl-2-methyleneindoline (Fischer base), oxindole, 3-methyl-1-phenyl-pyrazolin-5-one, indan-1,2-dione, indan-1,3-dione, indan-1-one, 2-amino-4-imino-1,3-thiazoline hydrochloride, benzoylacetonitrile, 3-dicyanomethyleneindan-1-one, 2-(2-furanoyl)acetonitrile, 2-(2-theonyl)acetonitrile, 2-(cyanomethyl)benzimidazole, 2-(cyanomethyl)benzothiazole and 2-(2,5-dimethyl-3-furanoyl)acetonitrile with physiologically compatible anions, particularly p-toluenesulfonates, methanesulfonates, hydrogen sulfates, tetrafluoroborates and halides, such as the chlorides, bromides and iodides.

In a third embodiment, the coloring agent additionally comprises at least one reaction product (hereafter named reaction product RP) as the substantive dye from a compound of Formula (I) and a compound of the component B. These types of reaction products RP can be obtained by e.g. heating both reactants in a neutral to weakly alkaline aqueous medium, wherein the reaction products RP either precipitate out of the solution as a solid or are isolated by evaporating the solution. The reaction products can also be prepared according to the literature method of H. Möhrle et al, *Pharmazie*, 1999, 54(4), 269-279.

For the synthesis of the reaction products RP, molar ratios of the component B to the compound according to Formula (I) of about 1:1 to about 2:1 can be reasonable.

The abovementioned compounds of Formula I, the compounds of component B, component C as well as the reaction products RP are preferably used in each case in an amount of 0.03 to 65 mmol, in particular, from 1 to 40 mmol, based on 100 g of the total coloring agent.

In addition, the inventive agents can comprise at least one developer component and optionally at least one coupler component as the oxidation dye precursors.

According to the invention, it may be preferred to use a p-phenylenediamine derivative or one of its physiologically compatible salts as the developer component. Particular preference is given to p-phenylenediamine derivatives of the formula (E1)

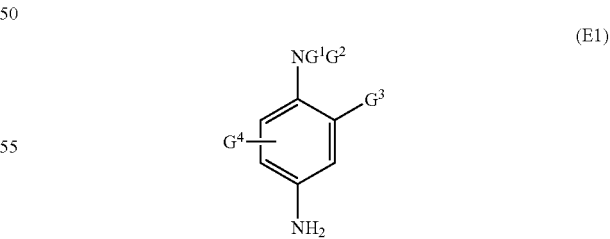

wherein
G$^1$ is a hydrogen atom, a C$_1$- to C$_4$ alkyl group, a C$_1$- to C$_4$ monohydroxyalkyl group, a C$_2$- to C$_4$ polyhydroxyalkyl group, a (C$_1$- to C$_4$) alkoxy(C$_1$- to C$_4$) alkyl group, a 4'-aminophenyl group or a C$_1$- to C$_4$ alkyl group that is substituted by a nitrogen-containing group, a phenyl group or a 4'-aminophenyl group;

$G^2$ is a hydrogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy($C_1$- to $C_4$) alkyl group or a $C_1$- to $C_4$ alkyl group that is substituted by a nitrogen-containing group;

$G^3$ is a hydrogen atom, a halogen atom, such as a chlorine, bromine, iodine or fluorine atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) hydroxyalkoxy group, a $C_1$- to $C_4$ acetylamino group, a $C_1$- to $C_4$ mesylamino alkoxy group or a $C_1$- to $C_4$ carbamoylaminoalkoxy group;

$G^4$ stands for a hydrogen atom, a halide atom or a $C_1$- to $C_4$ alkyl group or if $G^3$ und $G^4$ are in the ortho position relative to one another, they can together form a bridging a,ω-alkylenedioxo group, such as, for example, an ethylenedioxy group.

Examples of the $C_1$- to $C_4$ alkyl groups specified as substituents in the compounds according to the invention are the methyl, ethyl, propyl, isopropyl and butyl groups. Ethyl and methyl are preferred alkyl groups. Inventively preferred $C_1$- to $C_4$ alkoxy groups are a methoxy or ethoxy group, for example. Furthermore, preferred examples of a $C_1$- to $C_4$ hydroxyalkyl group that may be mentioned are a hydroxymethyl, a 2-hydroxyethyl, a 3-hydroxypropyl or a 4-hydroxybutyl group. A 2-hydroxyethyl group is particularly preferred. A particularly preferred $C_2$- to $C_4$ polyhydroxyalkyl group is the 1,2-dihydroxyethyl group. According to the invention, examples of halogen atoms are F, Cl or Br atoms, Cl atoms being quite particularly preferred. The other terms used are derived according to the invention from the definitions given here. Examples of nitrogen-containing groups of the formula (E1) are, in particular, the amino groups. $C_1$- to $C_4$ monoalkylamino groups, $C_1$- to $C_4$ dialkylamino groups, $C_1$- to $C_4$ trialkylamino groups, $C_1$- to $C_4$ monohydroxyalkylamino groups, imidazolinium and ammonium.

Particularly preferred p-phenylenediamines of the formula (E1) are chosen from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)-amino-2-methylaniline, 4-N,N-bis(β-hydroxyethyl)amino-2-chloroaniline, 2-(β-hydroxyethyl)-p-phenylenediamine, 2-α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine and 5,8-diaminobenzo-1,4-dioxane, and their physiologically compatible salts.

According to the invention, quite particularly preferred p-phenylenediamine derivatives of Formula (E1) are p-phenylenediamine, p-toluylenediamine, 2-(β-hydroxyethyl)-p-phenylenediamine, 2-(α,β-dihydroxyethyl)-p-phenylenediamine and N,N-bis-(β-hydroxyethyl)-p-phenylenediamine.

According to the invention, it may also be preferred to use compounds as the developer component, which comprise at least two aromatic nuclei that are substituted by amino and/or hydroxyl groups.

Among the binuclear developer components that can be used in the coloring agent compositions according to the invention, mention may be made in particular, of the compounds which conform to the following formula (E2), together with their physiologically compatible salts:

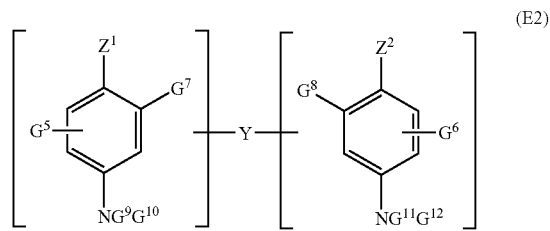

wherein:
$Z^1$ and $Z^2$, independently of one another, are a hydroxyl or $NH_2$ group, which is optionally substituted by a $C_1$- to $C_4$ alkyl group, by a $C_1$- to $C_4$ hydroxyalkyl group and/or by a bridge Y or which is optionally part of a bridging ring system, the bridge Y is an alkylene group having 1 to 14 carbon atoms, such as, for example, a linear or branched alkylene chain or an alkylene ring, which can be interrupted or terminated by one or more nitrogen-containing groups and/or one or more heteroatoms, such as oxygen, sulfur or nitrogen atoms and may possibly be substituted by one or more hydroxyl or $C_1$- to $C_8$ alkoxy groups, or a direct bond, $G^5$ und $G^6$, independently of one another, are a hydrogen or halogen atom, a $C_1$- to $C_4$ alkyl group, a $C_1$- to $C_4$ monohydroxyalkyl group, a $C_2$- to $C_4$ polyhydroxyalkyl group, a $C_1$- to $C_4$ aminoalkyl group or a direct bond to the bridge Y, $G^7$, $G^8$, $G^9$, $G^{10}$, $G^{11}$ and $G^{12}$, independently of one another, are a hydrogen atom, a direct bond to the bridge Y or a $C_1$- to $C_4$ alkyl group, with the proviso that the compounds of Formula (E2) comprise only one bridge Y per molecule.

According to the invention, the substituents in formula (E2) are defined analogously to the above statements.

Preferred binuclear developer components of the formula (E2) are, in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, 1,3-bis(2,5-diaminophenoxy)propan-2-ol, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Quite particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminophenyl)methane, 1,3-bis(2,5-diaminophenoxy)propan-2-ol, N,N'-bis(4'-aminophenyl)-1, 4-diazacycloheptane and 1,10-bis(2,5-diaminophenyl)-1,4,7,10-tetraoxadecane or one of their physiologically compatible salts.

Moreover, according to the invention, it may be preferred to use a p-phenylenediamine derivative or one of its physiologically compatible salts as the developer component. p-Aminophenol derivates of the Formula (E3) are particularly preferred.

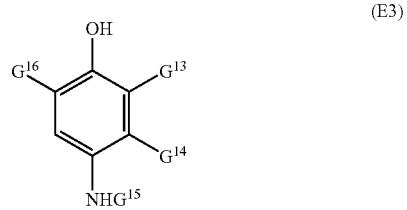

wherein:
- $G^{13}$ is a hydrogen atom, a halogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy-($C_1$- to $C_4$) alkyl group, a $C_1$- to $C_4$ aminoalkyl group, a hydroxy ($C_1$- to $C_4$) alkylamino group, a $C_1$- to $C_4$ hydroxyalkoxy group, a $C_1$- to $C_4$ hydroxyalkyl ($C_1$- to $C_4$) aminoalkyl group or a (di-$C_1$- to $C_4$ alkylamino) ($C_1$- to $C_4$) alkyl group, and
- $G^{14}$ is a hydrogen or halogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy-($C_1$- to $C_4$) alkyl group, $C_1$- to $C_4$ aminoalkyl group or a $C_1$- to $C_4$ cyanoalkyl group,
- $G^{15}$ stands for hydrogen, a $C_1$- to $C_4$ alkyl group, a $C_1$- to $C_4$ monohydroxyalkyl group, a $C_2$- to $C_4$ polyhydroxyalkyl group, a phenyl group or a benzyl group, and
- $G^{16}$ stands for hydrogen or a halogen atom.

According to the invention, the substituents in formula (E3) are defined analogously to the above statements.

Preferred p-aminophenols of the Formula (E3) are especially p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol together with their physiologically compatible salts.

Quite particularly preferred compounds of the Formula (E3) are p-aminophenol, 4-amino-3-methylphenol, 4-amino-2-aminomethylphenol, 4-amino-2-(α,β-dihydroxyethyl) phenol and 4-amino-2-(diethylaminomethyl)phenol.

Furthermore, the developer component can be selected from o-aminophenol and its derivatives, such as, for example 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazole-pyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese laid-open specification JP 02019576 A2 or in the laid-open specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3,843,892, DE 4,133,957 and patent applications WO 94/08969, WO 94/08970, EP 740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-di-amino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

Preferred pyrazolo pyrimidine derivatives are, in particular, the derivatives of the pyrazolo[1,5-a]pyrimidine of the following formula (E4) and its tautomeric forms provided there is a tautomeric equilibrium:

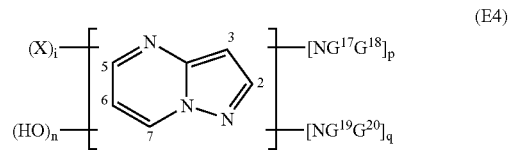

wherein:
- $G^{17}$, $G^{18}$, $G^{19}$ and $G^{20}$ independently of one another stand for a hydrogen atom, a $C_1$- to $C_4$ alkyl group, an aryl group, a $C_1$- to $C_4$ hydroxyalkyl group, a $C_2$- to $C_4$ polyhydroxyalkyl group a ($C_1$- to $C_4$) alkoxy ($C_1$- to $C_4$) alkyl group, a $C_1$- to $C_4$ aminoalkyl group, optionally protected by an acetyl-ureido or a sulfonyl group, a ($C_1$- to $C_4$) alkylamino ($C_1$- to $C_4$) alkyl group, a di-[($C_1$- to $C_4$) alkyl] ($C_1$- to $C_4$) aminoalkyl group, wherein the dialkyl groups optionally form a carbocycle or a heterocycle with 5 or 6 chain members, a $C_1$- to $C_4$ hydroxyalkyl or a di-($C_1$- to $C_4$) [hydroxyalkyl] ($C_1$- to $C_4$) aminoalkyl group,
- the X-groups independently of one another stand for a hydrogen atom, a $C_1$- to $C_4$ alkyl group, an aryl group, a $C_1$- to $C_4$ hydroxyalkyl group, a $C_2$- to $C_4$ polyhydroxyalkyl group a ($C_1$- to $C_4$) alkoxy ($C_1$- to $C_4$) alkyl group, a $C_1$- to $C_4$ aminoalkyl group, a ($C_1$- to $C_4$) alkylamino ($C_1$- to $C_4$) alkyl group, a di-[($C_1$- to $C_4$) alkyl] ($C_1$- to $C_4$) aminoalkyl group, wherein the dialkyl groups optionally form a carbocycle or a heterocycle with 5 or 6 chain members, a $C_1$- to $C_4$ hydroxyalkyl or a di-($C_1$- to $C_4$) [hydroxyalkyl] ($C_1$- to $C_4$) aminoalkyl group, an amino group, a $C_1$- bis $C_4$ alkyl or a di-($C_1$- to $C_4$) [hydroxyalkyl] ($C_1$- to $C_4$) amino group, a halogen atom, a carboxylic acid group or a sulfonic acid group.

i has the value 0, 1, 2 or 3,
p has the value 0 or 1,
q has the value 0 or 1 and
n has the value 0 or 1, with the proviso that
the sum of p+q is not equal to 0,
if p+q is equal to 2, then n has the value 0, and the groups $NG^{17}G^{18}$ and $NG^{19}G^{20}$ occupy the positions (2,3); (5,6); (6,7); (3,5) or (3,7);
if p+q is equal to 1, then n has the value 1, and the groups $NG^{17}G^{18}$ (or $NG^{19}G^{20}$) and the group OH occupy the positions (2,3); (5,6); (6,7); (3,5) or (3,7);

According to the invention, the substituents in formula (E4) are defined analogously to the above statements.

If the pyrazolo[1,5-a]pyrimidine of the above formula (E4) comprises a hydroxy group in one of the positions 2, 5 or 7 of the ring system, there is a tautomeric equilibrium, which is illustrated, for example, in the following scheme:

Among the pyrazolo[1,5-a]pyrimidines of the above formula (E4), mention may be made in particular, of:
Pyrazolo[1,5-a]pyrimidine-3,7-diamine;
2,5-Dimethylpyrazolo[1,5-a]pyrimidine-3,7-diamine;
Pyrazolo[1,5-a]pyrimidine-3,5-diamine;
2,7-Dimethyl-pyrazolo[1,5-a]pyrimidine-3,5-diamine;
3-Aminopyrazolo[1,5-a]pyrimidin-7-ol;
3-Aminopyrazolo[1,5-a]pyrimidin-5-ol;
2-(3-Aminopyrazolo[1,5-a]pyrimidin-7-ylamino)ethanol;
2-(7-Aminopyrazolo[1,5-a]pyrimidin-3-ylamino)ethanol;
2-[(3-Aminopyrazolo[1,5-a]pyrimidin-7-yl)-(2-hydroxyethyl)amino]ethanol;
2-[(7-Aminopyrazolo[1,5-a]pyrimidin-3-yl)-(2-hydroxyethyl)amino]ethanol;
5,6-Dimethylpyrazolo[1,5-a]pyrimidine-3,7-diamine;
2,6-Dimethylpyrazolo[1,5-a]pyrimidine-3,7-diamine;
3-Amino-7-dimethylamino-2, 5-dimethylpyrazolo[1,5-a]pyrimidine;

and their physiologically compatible salts and their tautomeric forms if a tautomeric equilibrium is present.

The pyrazolo[1,5-a]pyrimidines of the above formula (E4) can be prepared as described in the literature by cyclization starting from an aminopyrazole or from hydrazine.

In a further preferred embodiment, the dyeing compositions according to the invention comprise at least one coupler component m-Phenylenediamine derivatives, naphthol, resorcinol and resorcinol derivatives, pyrazolones and m-aminophenol derivatives are generally used as the coupling components. Particularly suitable coupling substances are 1-naphthol, 1,5-, 2,7-, and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,2-Methyl-4-chlor-5-aminophenol-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol und 2-methyl-4-chloro-5-aminophenol.

According to the invention, preferred coupler components are m-aminophenol and derivatives thereof such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trfluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, 1,3-dihydroxy-5-(methylamino)benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-[3-morpholin-4-ylphenyl)amino]ethanol, 3-amino-4-(2-methoxyethoxy)-5-methylphenylamine and 1-amino-3-bis-(2'-hydroxyethyl)aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1, 2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, pyrimidine derivatives, such as, for example 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives such as, for example, 1-hydroxy-3,4-methylenedioxybenzene, 1-amino-3,4-methylenedioxybenzene and 1-(2'-hydroxyethyl)amino-3,4-methylenedioxybenzene as well as their physiologically compatible salts.

According to the invention, particularly preferred coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol and 2,6-dihydroxy-3,4-dimethylpyridine.

Further, in the context of a fifth embodiment, the precursors of nature-analogous dyes that are used in the inventive agents are preferably those indoles and indolines, which have at least one hydroxyl or amino group, preferably as the substituent on the six-membered ring. These groups can carry further substituents, e.g., in the form of an etherified or esterified hydroxyl group or an alkylated amino group. In a second preferred embodiment, the coloring agents comprise at least one indole- or indoline derivative.

Derivatives of 5,6-dihydroxyindoline of the Formula (IIIa) are particularly well suited as precursors of nature-analogous hair dyes,

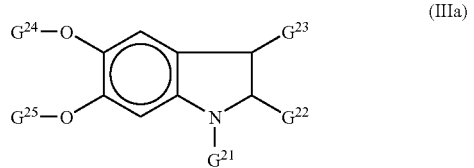

(IIIa)

in which, independently of one another $G^{21}$ stands for hydrogen, a $C_1$-$C_4$ alkyl group or a $C_1$-$C_4$ hydroxyalkyl group, $G^{22}$ stands for hydrogen or a —COOH group, where the —COOH group may also be present as the salt with a physiologically compatible cation, $G^{23}$ stands for hydrogen or a $C_1$-$C_4$ alkyl group, $G^{24}$ stands for hydrogen, a $C_1$-$C_4$ alkyl group or a —CO-$G^{26}$ group, in which $G^{26}$ stands for a $C_1$-$C_4$ alkyl group, and $G^{25}$ stands for one of the groups cited for $G^{24}$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, emphasis is placed particularly on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

In addition, derivatives of 5,6-hydroxyindole of the formula (IIIb) are exceptionally suitable as precursors of nature-analogous hair dyes,

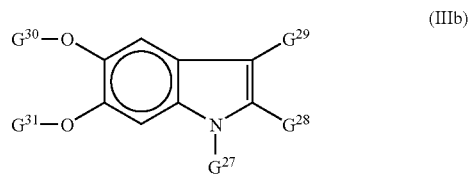

(IIIb)

in which, independently of one another $G^{27}$ stands for hydrogen, a $C_1$-$C_4$ alkyl group or a $C_1$-$C_4$ hydroxyalkyl group, $G^{28}$ stands for hydrogen or a —COOH group, where the —COOH group may also be present as the salt with a physiologically compatible cation, $G^{29}$ stands for hydrogen or a $C_1$-$C_4$ alkyl group, $G^{30}$ stands for hydrogen, a $C_1$-$C_4$ alkyl group or a —CO-$G^{32}$ group, in which $G^{32}$ stands for a $C_1$-$C_4$ alkyl group, and $G^{31}$ stands for one of the groups cited for $G^{30}$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is given to N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives can be employed in the inventive coloring agents both as free bases and also in the form of their physiologically compatible salts of inorganic or organic acids, e.g. the hydrochlorides, the sulfates and hydrobromides. The indole- or indoline derivatives are present in these coloring agents usually in amounts of from 0.05-10% by weight, preferably 0.2-5% by weight.

The presence of oxidizing agents, e.g. $H_2O_2$, can be dispensed with, particularly when the inventive agent does not comprise any oxidation dye precursors. If the inventive agent comprises air-oxidizable oxidation dye precursors or indole- or indoline derivatives, then in this case there is no problem with dispensing with oxidizing agents. However, in certain cases hydrogen peroxide or other oxidizing agents can be added to the inventive agent in order to produce nuances that are lighter than the keratinic fibers being dyed. Generally, oxidizing agents are employed in an amount of 0.01 to 6 wt. %, based on the application solution. A preferred oxidizing agent for human hair is $H_2O_2$. Mixtures of a plurality of oxidizing agents, such as for example a combination of hydrogen peroxide and peroxydisulfates of the alkali metals and alkaline earth metals or sources of iodine ions, such as e.g. alkali metal iodides and hydrogen peroxide or the above-mentioned peroxydisulfates, can also be used. According to the invention, the oxidizing agent or the combination of oxidizing agents together with oxidation catalysts can be used in the hair coloring agent. Oxidation catalysts are for example metal salts, metal chelate complexes or metal oxides, which permit an easy interchange between two oxidation states of the metal ions. Examples are salts, chelate complexes or oxides of iron, ruthenium, manganese and copper. Enzymes illustrate further possible oxidation catalysts. Suitable enzymes are, for example, peroxidases, which can considerably enhance the effect of small amounts of hydrogen peroxide. Also of suitability according to the invention are those enzymes, which directly oxidize the oxidation dye precursors with the help of atmospheric oxygen, such as, for example, the lactases, or which produce small amounts of hydrogen peroxide in situ and in so doing biocatalytically activate the oxidation of the dye precursors. Particularly suitable catalysts for the oxidation of the dye precursors are the so-called 2-electron oxidoreductases in combination with the substrates specific there for, e.g.

pyranose oxidase and e.g. D-glucose or galactose,
glucose oxidase and D-glucose,
glycerine oxidase and glycerine,
pyruvate oxidase and pyruvic acid or its salts,
alcohol oxidase and alcohol (MeOH, EtOH),
lactate oxidase and lactic acid or its salts,
tyrosinase oxidase and tyrosine,
uricase and uric acid or its salts,
choline oxidase and choline,
amino acid oxidase and amino acids.

In a sixth embodiment, in order to further modify the color nuances, the inventive coloring agents comprise, in addition to the inventively comprised compounds, further conventional substantive dyes, such as nitrophenylenediamine, nitroaminophenols, azo dyes, anthraquinones or indophenols. Preferred substantive dyestuffs are the compounds known under the international designations or trade names HC Yellow 2, HC Yellow 4, HC Yellow 5, HC Yellow 6, HC Yellow12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 as well as 1,4-diamino-2-nitrobenzene, 2-amino-4-nitrophenol, 1,4-bis(β-hydroxyethyl)amino-2-nitrobenzene, 3-nitro-4(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene.

In addition, the inventive agents can preferably comprise a cationic substantive dye. Particular preference is given here to
a) cationic triphenylmethane dyes, such as, for example, Basic Blue 7, Basic Blue 26, Basic Violet 2 and Basic Violet 14,
b) aromatic systems, which are substituted by a quaternary nitrogen group, such as, for example, Basic Yellow 57, Basic Red 76, Basic Blue 99, Basic Brown 16 and Basic Brown 17, and
c) substantive dyes, which comprise a heterocycle that has at least one quaternary nitrogen atom, as are specified, for example, in EP-A2-998 908 in the claims 6 to 11, which is explicitly incorporated herein by reference.

Preferred cationic substantive dyes of group (c) are, in particular, the following compounds:

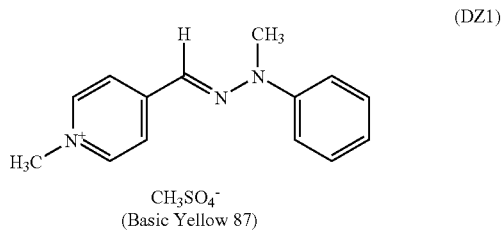
(DZ1)
(Basic Yellow 87)

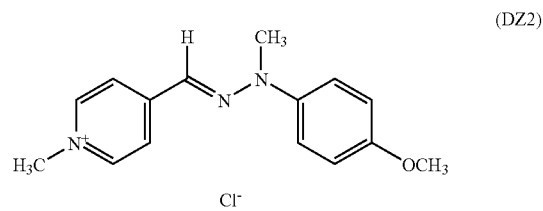
(DZ2)

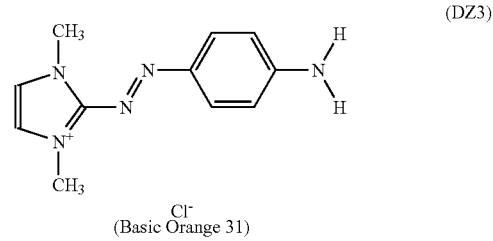
(DZ3)
(Basic Orange 31)

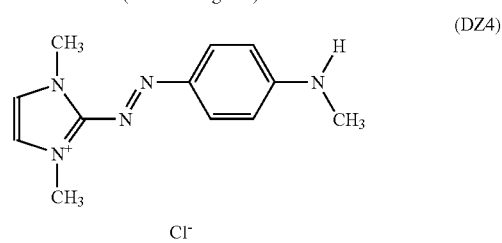
(DZ4)

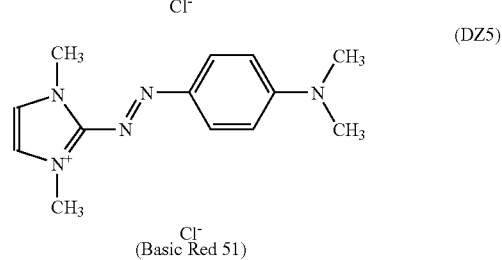
(DZ5)
(Basic Red 51)

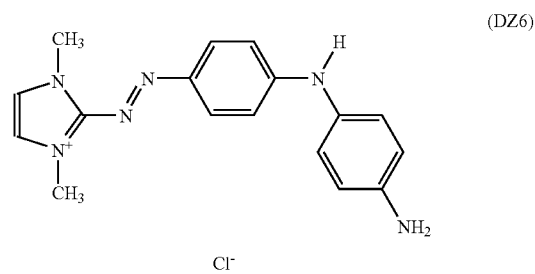
(DZ6)

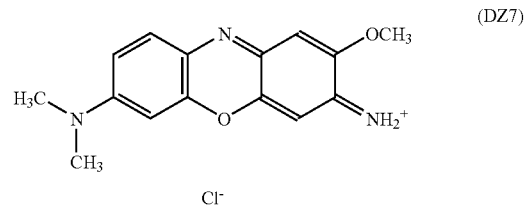
(DZ7)

-continued

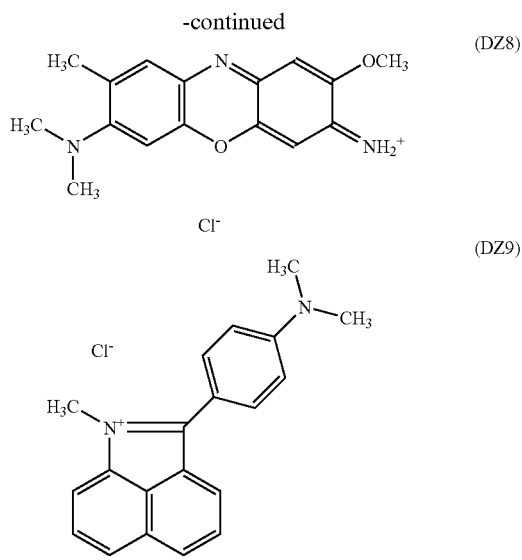

The compounds corresponding to the Formulas (DZ1), (DZ3) and (DZ5) are quite particularly preferred cationic substantive dyes of group (c). According to the invention, the cationic substantive dyes that are commercialized under the trade name Arianor®, are particularly preferred cationic substantive dyes.

The inventive compositions according to this embodiment comprise the substantive dyes preferably in a quantity of 0.01 to 20 wt. %, based on the total coloring agent.

In addition, the inventive preparations can also comprise naturally occurring dyestuffs as are for example, comprised in henna red, henna neutral, henna black, camomille leaves, sandalwood, black tea, alder buckthorn bark, sage, logwood, madder root, cashew, cedar and alkanet root.

It is not required that each of the optionally comprised substantive dyestuffs be pure compounds. In fact, the inventive coloring agents, due to the manufacturing processes for the individual dyestuffs, may comprise minor quantities of even more components, in so far as they have no detrimental influence on the coloration result or that they must be excluded on other, e.g. toxicological, grounds.

To obtain additional and more intensive colorations, the inventive agents can comprise additional color reinforcers. The color reinforcers are preferably selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, their derivatives and their physiologically compatible salts.

Each of the abovementioned color reinforcers can be added in an amount of 0.03 to 65 mmol, particularly 1 to 40 mmol, each based on 100 g of the total coloring agent.

The pH of the inventive agents can be pH 4 to 12, preferably pH 5 to 10.

The inventive coloring agents furnish intensive colorations already at physiologically compatible temperatures below 45° C. In consequence, they are particularly suitable for dyeing human hair. Usually, for use on human hair, the coloring agents can be incorporated into an aqueous cosmetic carrier. Suitable aqueous cosmetic carriers are, for example, creams, emulsions, gels or also surfactant-containing foaming solutions, such as, for example, shampoos or other preparations that are suitable for use on the keratinic fibers. If necessary, the coloring agents can also be incorporated into anhydrous carriers. Examples of further suitable and inventively preferred ingredients are given below.

In many cases the coloring agents comprise at least one surfactant, wherein, in principle, not only anionic, but also zwitterionic, ampholytic, non-ionic and cationic surfactants are suitable. However, in many cases it has proved advantageous to select the surfactants from among anionic, zwitterionic or non-ionic surfactants.

Suitable anionic surfactants for the inventive preparations are all anionic surface-active materials that are suitable for use on the human body. They are characterized by a water solubilizing anionic group, such as e.g. a carboxylate, sulfate, sulfonate or phosphate group, and a lipophilic alkyl group containing about 10 to 22 carbon atoms. In addition, the molecule may contain glycol- or polyglycol ether groups, ester, ether and amide groups as well as hydroxyl groups. Exemplary suitable anionic surfactants are each in the form of the sodium, potassium and ammonium as well as the mono-, di- and trialkanol ammonium salts with 2 or 3 carbon atoms in the alkanol group, linear fatty acids containing 10 to 22 carbon atoms (soaps),
ether carboxylic acids of the formula R—O—($CH_2$—$CH_2O)_x$—$CH_2$—COOH, in which R is a linear alkyl group with 10 to 22 carbon atoms and x=0 or 1 to 16,
acyl sarcosides with 10 to 18 carbon atoms in the acyl group,
acyl taurides with 10 to 18 carbon atoms in the acyl group,
acyl isethionates with 10 to 18 carbon atoms in the acyl group,
sulfosuccinic acid mono- and dialkyl esters with 8 to 18 carbon atoms in the alkyl group and sulfosuccinic acid mono-alkyl polyoxyethyl esters with 8 to 18 carbon atoms in the alkyl group and 1 to 6 oxyethylene groups,
linear alkane sulfonates with 12 to 18 carbon atoms,
linear alpha-olefin sulfonates with 12 to 18 carbon atoms
alpha-sulfo fatty acid methyl esters of fatty acids with 12 to 18 carbon atoms,
alkyl sulfates and alkyl polyglycol ether sulfates of formula R—O($CH_2$—$CH_2O)_x$—$SO_3H$, in which R is preferably a linear alkyl group with 10 to 18 carbon atoms and x=0 or 1 to 12,
mixtures of surface-active hydroxy sulfonates according to DE-A-37 25 030,
sulfated hydroxyalkyl polyethylene- and/or hydroxyalkylene propylene glycol ethers according to DE-A-37 23 354,
sulfonated unsaturated fatty acids with 12 to 24 carbon atoms and 1 to 6 double bonds according to DE-A-39 26 344,
esters of tartaric acid and citric acid with alcohols that represent the addition products of about 2 to 15 molecules of ethylene oxide and/or propylene oxide on fatty alcohols with 8 to 22 C atoms.

Preferred anionic surfactants are alkyl sulfates, alkyl polyglycol ether sulfates and ether carboxylic acids with 10 to 18 carbon atoms in the alkyl group and up to 12 glycol ether groups in the molecule, and especially salts of saturated and particularly unsaturated $C_8$-$C_{22}$ carboxylic acids, such as oleic acid, stearic acid, isostearic acid and palmitic acid.

Zwitterionic surfactants are designated as those surface-active compounds that carry at least one quaternary ammonium group and at least one —$COO^{(-)}$ or —$SO_3^{(-)}$ group in the molecule. Particularly suitable zwitterionic surfactants are the so-called betaines such as the N-alkyl-N,N-dimethyl ammonium glycinates, for example the cocoalkyl dimethyl ammonium glycinate, N-acylaminopropyl-N,N-dimethyl ammonium glycinates, for example the cocoacylaminopropyl dimethyl ammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative, known under the CTFA name cocoamidopropyl betaine.

The ampholytic surfactants are understood to include such surface-active compounds that apart from a $C_{8-18}$ alkyl or acyl group, comprise at least one free amino group and at least one COOH or $SO_3H$ group in the molecule, and are able to form internal salts. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylaminopropionic acids and alkylamino acetic acids, each with about 8 to 18 carbon atoms in the alkyl group. Particularly preferred ampholytic surfactants are N-cocoalkylamino propionate, the cocoacylaminoethylamino propionate and the $C_{12-18}$ acyl sarcosine.

Non-ionic surfactants comprise e.g. a polyol group, a polyalkylene glycol ether group or a combination of polyol- and polyglycol ether groups as the hydrophilic group. Exemplary compounds of this type are
- addition products of 2 to 30 moles ethylene oxide and/or 0 to 5 moles propylene oxide to linear fatty alcohols with 8 to 22 carbon atoms, to fatty acids with 12 to 22 carbon atoms and to alkyl phenols with 8 to 15 carbon atoms in the alkyl group,
- $C_{12-22}$ fatty acid mono and diesters of addition products of 1 to 30 moles ethylene oxide on glycerine;
- $C_{8-22}$ alkyl mono- and oligoglycosides and their ethoxylated analogs,
- addition products of 5 to 60 moles ethylene oxide on castor oil and hydrogenated castor oil,
- addition products of ethylene oxide on sorbitan fatty acid esters
- addition products of ethylene oxide on fatty acid alkanolamides.

Examples of the cationic surfactants that can be used in the inventive hair treatment agents are especially quaternary ammonium compounds. Ammonium halides such as alkyl trimethyl ammonium chlorides, dialkyl dimethyl ammonium chlorides and trialkyl methyl ammonium chloride are preferred, e.g. cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. The quaternized protein hydrolyzates illustrate further inventively usable cationic surfactants.

Cationic silicone oils, such as, for example, the commercially available products Q2-7224 (manufacturer: Dow Corning; a stabilized trimethylsilylamodimethicone), Dow Corning 929 emulsion (comprising a hydroxylamino modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80) are similarly suitable according to the invention.

Alkylamido amines, particularly fatty acid amido amines such as stearylamidopropyldimethylamine, available under the name Tego Amid®S 18, are characterized by a good conditioning action, especially by their good biodegradability.

Quaternary ester compounds, so called "esterquats", such as methyl hydroxyalkyl dialkoyloxyalkyl ammonium methosulfates, commercialized under the trade name Stepantex®, also possess very good biodegradability.

An example of a suitable cationic surfactant quaternary sugar derivative is the commercial product Glucquat® 100, a "lauryl methyl gluceth-10 hydroxypropyl dimonium chloride" according to CFTA nomenclature.

For compounds with alkyl groups that are used as surfactants, they may each be pure substances. However, it is normally preferred to start with natural vegetal or animal raw materials for the manufacture of these materials, with the result that mixtures of substances are obtained, which have different alkyl chain lengths that depend on each raw material.

For surfactants, which are represented by the addition products of ethylene oxide and/or propylene oxide to fatty alcohols or derivatives of these addition products, both products with a "normal" homolog distribution as well as those with a narrow homolog distribution may be used. The term "normal" homolog distribution is understood to mean mixtures of homologs obtained from the reaction of fatty alcohols and alkylene oxide using alkali metals, alkali metal hydroxides or alkali metal alcoholates as catalysts. On the other hand, narrow homolog distributions are obtained if e.g. hydrotalcite, alkaline earth metal salts of ether carboxylic acids, alkaline earth metal oxides, hydroxides or alcoholates are used as catalysts. The use of products with a narrow homolog distribution can be preferred.

Further exemplary active products, auxiliaries and additives are
- non-ionic polymers, such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers, polysiloxanes with quaternary groups, dimethyl diallyl ammonium chloride polymers, acrylamide-dimethyl diallyl ammonium chloride copolymers, dimethylaminoethyl methacrylate-vinyl pyrrolidone copolymers quaternized with diethyl sulfate, vinyl pyrrolidone-imidazolinium methochloride copolymers and quaternized polyvinyl alcohol,
- zwitterionic and amphoteric polymers, such as, for example, acrylamidopropyl trimethyl ammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers,
- thickeners like agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives of amylose, amylopectin and dextrins, clays such as e.g. bentonite or synthetic hydrocolloids such as e.g. polyvinyl alcohol,
- structurants such as glucose and maleic acid,
- hair conditioning compounds like phospholipids, for example soya lecithin, egg lecithin and cephalin, as well as silicone oils, protein hydrolyzates, particularly those of elastin, collagen, keratin, milk protein, soya protein and wheat protein, their condensation products with fatty acids as well as quaternized protein hydrolyzates, perfume oils, dimethyl isosorbitol and cyclodextrins, solubilizers, such as ethanol, isopropanol, ethylene glycol, propylene glycol, glycerine and diethylene glycol, anti-dandruff active materials like piroctone olamine and zinc omadine, additional substances for adjusting the pH, such as ammonia, monoethanolamine, basic amino acids and citric acid active ingredients, such as panthenol, pantothenic acid, allantoin, pyrrolidone carboxylic acids and salts thereof, plant extracts and vitamins, cholesterol, UV stabilizers, thickeners like sugar esters, polyol esters or polyol alkyl ethers, fats and waxes like spermaceti, beeswax, montan wax, paraffins, fatty alcohols and fatty acid esters, fatty acid alkanolamides, chelating agents like EDTA, NTA and phosphonic acids, swelling and penetration agents such as glycerol, propylene glycol monoethyl ether, carbonates, hydrogen carbonates, guanidines, ureas, and primary, secondary and tertiary phosphates, imidazoles, tannins, pyrrole, opacifiers like latex, pearlizers like ethylene glycol mono and distearate, blowing agents like propane-butane mixtures, $N_2O$, dimethyl ether, $CO_2$ and air, as well as antioxidants.

The ingredients of the hydrated carrier are added in the usual amounts for the purpose of manufacturing the inventive coloring agent, e.g. emulsifiers are added in concentrations of 0.5 to 30 wt. % and thickeners in concentrations of 0.1 to 25 wt. % of the total coloring agent.

For the color result it can be advantageous to add ammonium or metal salts to the coloring agents. Suitable metal salts are e.g. formates, carbonates, halides, sulfates, butyrates, valeriates, capronates, acetates, lactates, glycolates, tartrates, citrates, gluconates, propionates, phosphates and phosphonates of alkali metals, like potassium, sodium or lithium, alkaline earth metals, such as magnesium, calcium, strontium or barium, or of aluminum, manganese, iron, cobalt, copper or zinc, wherein sodium acetate, lithium bromide, calcium bromide, calcium gluconate, zinc chloride, zinc sulfate, magnesium chloride, magnesium sulfate, ammonium carbonate, -chloride and -acetate are preferred. These salts are preferably comprised in an amount of 0.03 to 65 mmol, particularly 1 to 40 mmol, based on 100 g of the total coloring agent.

The pH of the ready-for-use color preparations is normally between 2 and 11, preferably between 5 and 10.

A second subject matter of the present invention relates to the use as the coloring component in hair dyes of at least one compound corresponding to Formula I and/or its enamine form,

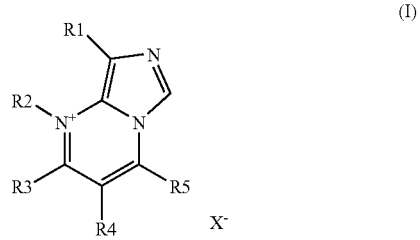

wherein $R^1$, $R^2$, $R^3$, $R^4$, $R^5$ and $X^-$ are as defined in the first subject matter of the invention, together with at least one reactive carbonyl compound as the component B.

In a preferred embodiment, those compounds corresponding to Formula I are used as the coloring component in hair dyes, which are selected from the preferred and particularly preferred representatives cited in the first subject matter.

Moreover, it can be preferred to use at least one reaction product RP from a compound corresponding to Formula I and a representative of the component B as the coloring component in hair dyes.

A third subject matter of the present invention relates to a method for coloring fibers containing keratin, especially human hair, wherein a coloring agent, comprising at least one compound corresponding to Formula I and/or its enamine form,

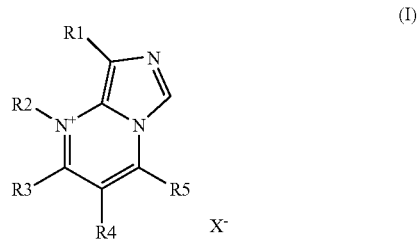

wherein $R^1$, $R^2$, $R^3$, $R^4$, $R^5$ and $X^-$ are as defined in the first subject matter of the invention, together with at least one reactive carbonyl compound as the component B, is applied onto the keratin-containing fibers for some time, normally ca. 15-30 minutes, left on the fibers and subsequently rinsed out again or washed out with a shampoo. During the contact time of the agent with the fibers, it can be advantageous to support the coloring process by applying heat. The supply of heat can be from a heat source, such as e.g. warm air from a stream of warm air, as also, especially for a hair coloration on living subjects, from the body temperature of the subject. For the latter alternative, the areas being dyed are normally covered with a cap.

Accordingly, the compounds corresponding to Formula I and the compounds of component B, particularly their preferred and particularly preferred representatives cited above, are applied as the coloring components either simultaneously onto the hair or else consecutively, i.e. in a multi-step method, wherein it is irrelevant which component is applied first. The optionally comprised ammonium or metal salts can be added to the compounds of Formula I or to the compounds of component B. There can be an interval of up to 30 minutes between the addition of the individual components. A pretreatment of the fibers with the salt solution is also possible.

Before using the inventive agent in the inventive method, it can be desirable to subject the keratin-containing fibers being dyed to a pre-treatment. The time sequence for the required pre-treatment step and the application of the inventive agent does not have to be immediately one after the other, rather the interval between the pre-treatment step and the application of the inventive agent can be up to two weeks at most. There are many methods of pre-treatment. Preferably, the fiber is subjected to V1 bleaching prior to the application of the inventive agent V2 oxidative coloration prior to the application of the inventive agent.

In the context of the pre-treatment V1, the keratin-containing fiber is treated with a hair bleaching composition. In addition to an oxidizing agent, such as hydrogen peroxide, the hair bleaching composition preferably comprises at least one inorganic peroxy salt that acts as the oxidation and bleach booster, such as e.g. a peroxysulfate of sodium, potassium or ammonium. Colorations according to the inventive method acquire a particular brilliance and color depth as a result of the pre-treatment V1.

In the context of the pre-treatment V2, an agent comprising abovementioned oxidation dye precursors as the developer components and optional coupler components as well as optional abovementioned derivatives of indole or indoline, is applied onto the fiber, and after a contact time, optionally with the addition of abovementioned oxidizing agents on the hair, is left for 5-45 minutes on the keratin fiber. The hair is then rinsed. The existing oxidation colorations can be given a new color nuance by the subsequent application of the inventive agent. By choosing the color nuance of the inventive agent in the same color nuance of the oxidative coloration, then the coloration of the existing oxidation coloration can be refreshed in accordance with the inventive method. It can be seen that the color refreshing or nuancing according to the inventive method is superior in color brilliance and color depth to a color refreshing or nuancing effected solely with conventional substantive dyes.

If in addition to the compounds according to Formula I and the compounds of component B, the hair dye comprises hydrogen peroxide as the oxidizing agent or a hydrogen peroxide-containing oxidizing agent mixture, then the pH of the hydrogen peroxide-containing hair dye is preferably in a pH range of pH 7 to pH 11, preferably pH 8 to pH 10. The oxidizing agent can be mixed with the hair dye immediately prior to use and applied to the hair. If the compounds of Formula I and the component B are to be applied in a two-step method onto the hair, then the oxidizing agent is used in one of the two steps with the corresponding dyeing component. For this purpose, it can be preferred to package the oxidizing agent with one of the dye components in one container.

The compounds according to Formula I and the compounds of component B can be stored either in separate containers or together in one container, either in a liquid to pasty preparation (aqueous or anhydrous) or as a solid, for example as a dry powder. If the components are stored together in a liquid preparation then they should be essentially anhydrous and have an acid pH in order to diminish any reaction of the components. If the components are stored together, then it is preferred to present them as solids, in particular in the form of a preferably multi-layer molded body, e.g. as a tablet. In the case of multi-layered molded bodies, the component A is incorporated into one layer and the component B into another, wherein a further layer preferably lies between the layers as the separation layer. The separation layer is free of compounds of the components A and B.

When stored separately, the reactive components are first intimately blended together immediately prior to use. With dry storage, a defined quantity of warm (30° C. to 80° C.) water is normally added before use to prepare a homogeneous mixture.

A fourth subject matter of the invention is the use of at least one compound corresponding to Formula I and/or its enamine form,

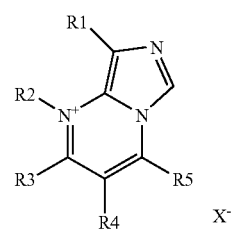

(I)

wherein $R^1$, $R^2$, $R^3$, $R^4$, $R^5$ and $X^-$ are as defined in the first subject matter of the invention, together with at least one reactive carbonyl compound as the component B to nuance the oxidation colorations of keratin-containing fibers, especially human hair. For use, it is irrelevant whether the nuancing is carried out simultaneously with the oxidative coloration or the oxidative coloration is done before the nuancing.

A fifth subject matter of the invention is the use of at least one compound corresponding to Formula I and/or its enamine form,

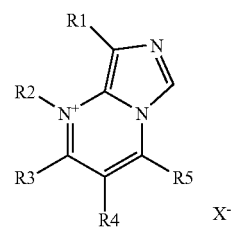

(I)

wherein $R^1$, $R^2$, $R^3$, $R^4$, $R^5$ and $X^-$ are as defined in the first subject matter of the invention, together with at least one reactive carbonyl compound as the component B to refresh the color of keratin-containing fibers that were dyed with oxidative coloring agents.

The colorations of keratin-containing fibers are known to be exposed to environmental influences, such as light, rubbing or washing and can thus lose their brilliance and color depth. In the worst of cases a shift in the nuance of the coloration sometimes occurs. Such changed colorations of keratin-containing fibers can be shifted back, when desired, by a color refreshment to the approximate color state present immediately after the original coloration. According to the invention, a combination of at least one compound of Formula I and at least one compound of component B is used for such a color refreshment.

EXAMPLES 1.0 Synthesis of 1,2,4-trimethyl-8-[(methylamino) carbonyl]imidazo[1,5-a]pyrimidinium chloride $1^{st}$ Step:

Synthesis of N-methyl-4-(methylamino)-1H-imidazol-5-carboxamide (Theophyllidine), hydrochloride Theophylline, 50.0 g (0.275 mol), was heated in 250 ml 50% conc. potassium hydroxide solution for ca. 6 hours. The reaction solution was filtered hot. On cooling the filtrate, a precipitate was formed, which was filtered off. The solid was dissolved in water and then acidified to pH 1 with concentrated hydrochloric acid. A precipitate again formed, which after filtration was washed with water. Purification can be effected by recrystallization from methanol.

Yield: 48.0 g (92%) Melting point: 204-206° C.

2$^{nd}$ Step:

Synthesis of 1,2,4-trimethyl-8-[(methylamino)carbonyl]imidazo[1,5-a]pyrimidinium chloride (see Formula II, below)

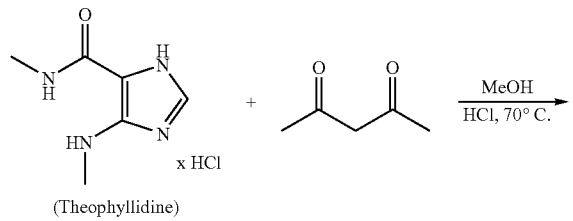

(Theophyllidine)

(II)

Theophyllidine (hydrochloride), 27.0 g (0.142 mol), from step 1, was heated in 1400 ml methanol under reflux for 5 hours with acetylacetone, 28.7 g (0.284 mol), and 20 g concentrated hydrochloric acid. The solvent was then removed on the rotary evaporator and the yellow residue was purified by recrystallization from ethanol/diethyl ether.

Yield: 33.5 g (93%) M. pt.: 180° C.

2.0 Preparation of the Coloring Agent

| Aqueous gel formulation for component A | Gel 1: |
|---|---|
| CH-acidic compound (component A) | 10 mmol |
| Natrosol HR 250 | 2 g |
| Water, deionized | ad 100 g |

The CH-acidic compound (component A) was firstly dissolved in a little water with stirring and then filled up to 98 g with water. The Natrosol was added with stirring and the end of the swelling process awaited.

| Aqueous gel formulation for component B | Gel 2: |
|---|---|
| Carbonyl compound (component B) | 10 mmol |
| Natrosol HR 250 | 2 g |
| NaOH (50% aqueous solution) | if necessary a few drops |
| Water, deionized | ad 100 g |

The carbonyl compound (component B) was dissolved or suspended in a little water. When needed, the solubility was increased by alkalization with a few drops of 50% sodium hydroxide solution. Subsequently, water was added to fill up to 98 g and stirring continued to complete the dissolution of the carbonyl compound (with partial gentle heating to ca. 40° C.). Finally, the Natrosol was added with stirring and the swelling process awaited.

3.0 Colorations

Aqueous gel formulations were prepared from point 2.0 (gel 1 and gel 2) with the dye precursor combinations of Table 1. The gels were mixed in the weight ratio 1:1, and then the pH was adjusted to 6 or 8 (see Table 1) with ammonia or tartaric acid. The dye precursors were used in the combinations that are listed in Table 1.

The resulting ready-for-use hair dye was applied on a strand of 90% grayed, unpretreated human hair (liquid weight ratio: gel mixture to hair=2 to 1) and evenly dispersed with an applicette. After a contact time of 30 minutes at 32° C., the strands were rinsed out with lukewarm water and then dried in a stream of warm air (30° C. to 40° C.). The colorations were assessed under a daylight lamp. The coloration results are to be found in Table 1.

TABLE 1

| Component A (gel 1) | Component B (gel 2) | pH | Color tone |
|---|---|---|---|
| A1 | B1 | 6 | intense red violet |
| A1 | B1 | 8 | light red violet |
| A1 | B2 | 6 | intense blue |
| A1 | B2 | 8 | pastel blue |
| A1 | B3 | 6 | intense dark blue |
| A1 | B3 | 8 | light blue/turquoise |
| A1 | B4 | 6 | dark greeny blue |
| A1 | B4 | 8 | turquoise |
| A1 | B5 | 6 | bright violet |
| A1 | B5 | 8 | pale violet |
| A1 | B6 | 6 | intense dark blue |
| A1 | B6 | 8 | medium blue |
| A1 | B7 | 6 | intense browny red |
| A1 | B7 | 8 | pale browny red |

What is claimed is:

1. A composition comprising:
   (i) at least one component A comprising a compound selected from the group consisting of imidazo[1,5-a]pyrimidinium derivatives of general formula I, enamine counterparts of imidazo[1,5-a]pyrimidinium derivatives of the general formula I, and mixtures thereof:

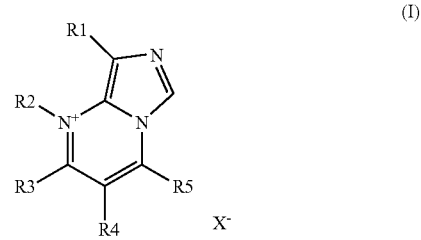

wherein $R^1$ represents a substituent selected from the group consisting of a hydrogen atom, a halogen atom, a carboxyl group, a ($C_1$-$C_6$) alkoxy group, a ($C_1$-$C_6$) alkyl group, a ($C_2$-$C_6$) alkenyl group, an optionally substituted aryl group, an aryl ($C_1$-$C_6$) alkyl group, a ($C_2$-$C_6$) hydroxyalkyl group, a ($C_2$-$C_6$) polyhydroxyalkyl group, and a $R^I R^{II} N$—CO— group, wherein $R^I$ and $R^{II}$ each independently represent a substituent selected from the group consisting of a hydrogen atom, a ($C_1$-$C_6$) alkyl group, a ($C_1$-$C_6$) alkenyl group, an aryl group, and an aryl $C_1$-$C_6$ alkyl group, and wherein $R^I$ and $R^{II}$ together with the nitrogen atom in the $R^I R^{II} N$—CO— group can form a 5-7 membered ring;

wherein $R^2$ represents a substituent selected from the group consisting of a ($C_1$-$C_6$) alkyl group, a ($C_2$-$C_6$) alkenyl group, an optionally substituted aryl group, an aryl ($C_1$-$C_6$) alkyl group, a ($C_1$-$C_6$) hydroxyalkyl group, a ($C_2$-$C_6$) polyhydroxyalkyl group, and a $R^{III} R^{IV} N$—($CH_2$)$_n$— group, wherein $R^{III}$ and $R^{IV}$ each independently represent a hydrogen atom, a ($C_1$-$C_6$) alkyl group, a ($C_1$-$C_6$) alkenyl group, and an aryl $C_1$-$C_6$ alkyl group, and wherein $R^{III}$ and $R^{IV}$ together with the nitrogen atom in the $R^{III} R^{IV} N$—($CH_2$)$_n$— group can form a 5-7 membered ring, and wherein n represents and integer of 2 to 6;

wherein $R^3$ and $R^5$ each independently represents a substituent selected from the group consisting of a hydrogen atom, a ($C_1$-$C_6$) alkyl group, a ($C_2$-$C_6$) alkenyl group, an aryl group, an aryl ($C_1$-$C_6$) alkyl group, a ($C_2$-$C_6$) hydroxyalkyl group, and a ($C_2$-$C_6$) polyhydroxyalkyl group, with the proviso that at least one of $R^3$ and $R^5$ represents a methyl group;

wherein $R^4$ represents a substituent selected from the group consisting of a hydrogen atom, a ($C_1$-$C_6$) alkyl group, a ($C_2$-$C_6$) alkenyl group, a ($C_1$-$C_6$) hydroxyalkyl group, a ($C_2$-$C_6$) polyhydroxyalkyl group, and an optionally substituted aryl group; and wherein $X^-$ represents a physiologically compatible anion; and (ii) at least one component B comprising a reactive carbonyl compound.

2. The composition according to claim 1, wherein $R^I$ represents a $R^I R^{II} N$—CO— group, wherein $R^I$ and $R^{II}$ each independently represents a substituent selected from the group consisting of a hydrogen atom and a ($C_1$-$C_6$) alkyl group.

3. The composition according to claim 1, wherein the at least one component A comprises a salt of $X^-$ and a cation selected from the group consisting of 1,2,4-trimethyl-8-[(methylamino)carbonyl]imidazo[1,5-a]pyrimidinium, 1,2,3,4-tetramethyl-8-[(methylamino)carbonyl]imidazo[1,5-a]pyrimidinium, 3-ethyl-1,2,4-trimethyl-8-[(methylamino)carbonyl]imidazo[1,5-a]pyrimidinium, counterpart enamines forms thereof, and mixtures thereof.

4. The composition according to claim 1, wherein the at least one component B comprises a compound of the general formula (Ca-1):

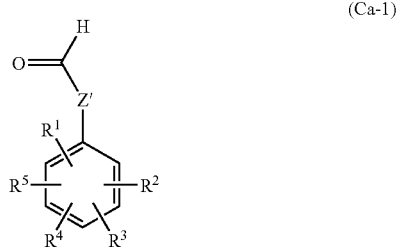

(Ca-1)

wherein $R^1$, $R^2$ and $R^3$ each independently represent a substituent selected from the group consisting of a hydrogen atom, a halogen atom, a $C_1$-$C_6$ alkyl group, a hydroxyl group, a $C_1$-$C_6$ alkoxy group, a $C_1$-$C_6$ dialkylamino group, a di($C_2$-$C_6$ hydroxyalkyl)amino group, a di($C_1$-$C_6$ alkoxy $C_1$-$C_6$ alkyl) amino group, a $C_1$-$C_6$ hydroxyalkyloxy group, a sulfonyl group, a carboxyl group, a sulfonic acid group, a sulfonamido group, a sulfonamide group, a carbamoyl group, a $C_2$-$C_6$ acyl group, an acetyl group, and a nitro group; wherein Z' represents a direct bond or a vinylene group; and wherein $R^4$ and $R^5$ each represent a hydrogen atom or together form a 5- or 6-membered aromatic or aliphatic ring with the aromatic ring to which $R^4$ and $R^5$ are bound.

5. The composition according to claim 2, wherein the at least one component B comprises a compound of the general formula (Ca-1):

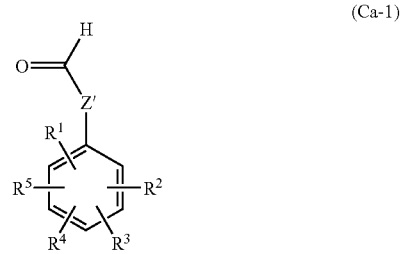

(Ca-1)

wherein $R^1$, $R^2$ and $R^3$ each independently represent a substituent selected from the group consisting of a hydrogen atom, a halogen atom, a $C_1$-$C_6$ alkyl group, a hydroxyl group, a $C_1$-$C_6$ alkoxy group, a $C_1$-$C_6$ dialkylamino group, a di($C_2$-$C_6$ hydroxyalkyl)amino group, a di($C_1$-$C_6$ alkoxy $C_1$-$C_6$ alkyl) amino group, a $C_1$-$C_6$ hydroxyalkyloxy group, a sulfonyl group, a carboxyl group, a sulfonic acid group, a sulfonamido group, a sulfonamide group, a carbamoyl group, a $C_2$-$C_6$ acyl group, an acetyl group, and a nitro group; wherein Z' represents a direct bond or a vinylene group; and wherein $R^4$ and $R^5$ each represent a hydrogen atom or together form a 5- or 6-membered aromatic or aliphatic ring with the aromatic ring to which $R^4$ and $R^5$ are bound.

6. The composition according to claim 1, wherein the at least one component B comprises an aldehyde selected from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitro-salicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-(1-imidazolyl)benzaldehyde, piperonal, and mixtures thereof.

7. The composition according to claim 1, further comprising at least one component C comprising a CH-acidic compound, wherein the CH-acidic compound is different from the at least one component A.

8. The composition according to claim 5, further comprising at least one component C comprising a CH-acidic compound, wherein the CH-acidic compound is different from the at least one component A.

9. The composition according to claim 7, wherein the CH-acidic compound comprises a salt of a physiologically compatible anion and a cation selected from the group consisting of 1,4-dimethylquinolinium, 1-ethyl-4-methylquinolinium, 1-ethyl-2-methylquinolinium, 1,2,3,3-tetramethyl-3H-indolium, 2,3-dimethylbenzothiazolium, 2,3-dimethyl-naphtho[1,2-d]thiazolium, 3-ethyl-2-methyl-naphtho[1,2-d]thiazolium, 3-ethyl-2-methyl-benzoxazolium, 1,2,3-trimethylquinoxalinium, 3-ethyl-2-methylbenzothiazolium, 1,2-dihydro-1,3,4,6-tetramethyl-2-oxopyrimidinium, 1,2-dihydro-1,3,4-trimethyl-2-oxo-pyrimidinium, 1,2-dihydro-4,6-dimethyl-1,3-dipropyl-2-oxopyrimidinium, 1,2-dihydro-1,3,4,6-tetramethyl-2-thioxopyrimidinium, 1,2-dihydro-1,3,4,5,6-pentamethyl-2-oxopyrimidinium, 2,5-dimethyl-3-(2-propenyl)-1,3,4-thiadiazolium, 3-ethyl-2,5-dimethyl-1,3,4-thiadiazolium, 1,2-dimethylquinolinium and 1,3,3-trimethyl-2-methyleneindoline (Fischer base), oxindole, 3-methyl-1-phenyl-pyrazolin-5-one, indan-1,2-dione, indan-1,3-dione, indan-1-one, 2-amino-4-imino-1,3-thiazoline hydrochloride, benzoylacetonitrile, 3-dicyanomethyleneindan-1-one, 2-(2-furanoyl)acetonitrile, 2-(2-theonyl)acetonitrile, 2-(cyanomethyl)benzimidazole, 2-(cyanomethyl)benzothiazole, 2-(2,5-dimethyl-3-furanoyl)acetonitrile, and mixtures thereof.

10. The composition according to claim 1, wherein the at least one component A and the at least one component B are each present in an amount of 0.03 to 65 mmol, based on 100 g of the composition.

11. The composition according to claim 7, wherein the at least one component A, the at least one component B and the at least one component C are each present in an amount of 0.03 to 65 mmol, based on 100 g of the composition.

12. The composition according to claim 1, further comprising a color reinforcer selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, and mixtures thereof.

13. The composition according to claim 1, further comprising an oxidizing agent.

14. The composition according to claim 1, further comprising an oxidation dye precursor selected from the group consisting of developer components, coupler components, and mixtures thereof.

15. The composition according to claim 1, further comprising a substantive dye.

16. The composition according to claim 1, further comprising a surfactant selected from the group consisting of anionic surfactants, zwitterionic surfactants, non-ionic surfactants, and mixtures thereof.

17. A method comprising:
(a) providing at least one component A comprising a compound selected from the group consisting of imidazo[1,5-a]pyrimidinium derivatives of general formula I, enamine counterparts of imidazo[1,5-a]pyrimidinium derivatives of the general formula I, and mixtures thereof:

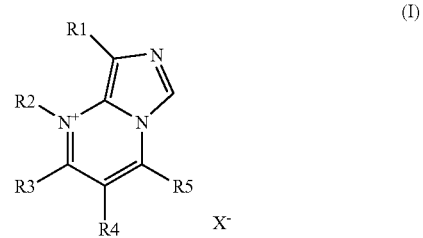

wherein $R^1$ represents a substituent selected from the group consisting of a hydrogen atom, a halogen atom, a carboxyl group, a $(C_1-C_6)$ alkoxy group, a $(C_1-C_6)$ alkyl group, a $(C_2-C_6)$ alkenyl group, an optionally substituted aryl group, an aryl $(C_1-C_6)$ alkyl group, a $(C_2-C_6)$ hydroxyalkyl group, a $(C_2-C_6)$ polyhydroxyalkyl group, and a $R^I R^{II} N$—CO— group, wherein $R^I$ and $R^{II}$ each independently represent a substituent selected from the group consisting of a hydrogen atom, a $(C_1-C_6)$ alkyl group, a $(C_1-C_6)$ alkenyl group, an aryl group, and an aryl $C_1-C_6$ alkyl group, and wherein $R^I$ and $R^{II}$ together with the nitrogen atom in the $R^I R^{II} N$—CO— group can form a 5-7 membered ring;

wherein $R^2$ represents a substituent selected from the group consisting of a $(C_1-C_6)$ alkyl group, a $(C_2-C_6)$ alkenyl group, an optionally substituted aryl group, an aryl $(C_1-C_6)$ alkyl group, a $(C_1-C_6)$ hydroxyalkyl group, a $(C_2-C_6)$ polyhydroxyalkyl group, and a $R^{III} R^{IV} N$—$(CH_2)_n$— group, wherein $R^{III}$ and $R^{IV}$ each independently represent a hydrogen atom, a $(C_1-C_6)$ alkyl group, a $(C_1-C_6)$ alkenyl group, and an aryl $C_1-C_6$ alkyl group, and wherein $R^{III}$ and $R^{IV}$ together with the nitrogen atom in the $R^{III} R^{IV} N$—$(CH_2)_n$— group can form a 5-7 membered ring, and wherein n represents and integer of 2 to 6;

wherein $R^3$ and $R^5$ each independently represents a substituent selected from the group consisting of a hydrogen atom, a $(C_1-C_6)$ alkyl group, a $(C_2-C_6)$ alkenyl group, an aryl group, an aryl $(C_1-C_6)$ alkyl group, a $(C_2-C_6)$ hydroxyalkyl group, and a $(C_2-C_6)$ polyhydroxyalkyl group, with the proviso that at least one of $R^3$ and $R^5$ represents a methyl group;

wherein $R^4$ represents a substituent selected from the group consisting of a hydrogen atom, a $(C_1-C_6)$ alkyl group, a $(C_2-C_6)$ alkenyl group, a $(C_1-C_6)$ hydroxyalkyl group, a $(C_2-C_6)$ polyhydroxyalkyl group, and an optionally substituted aryl group; and wherein $X^-$ represents a physiologically compatible anion;

(b) providing at least one component B comprising a reactive carbonyl compound;

(c) contacting a keratinic fiber with the at least one component A and the at least one component B; and (d) removing the at least one component A and the at least one component B from the keratinic fiber.

18. The method according to claim 17, wherein the at least one component A and the at least one component B are applied to the keratinic fiber simultaneously.

19. The method according to claim 17, wherein the at least one component A and the at least one component B are applied to the keratinic fiber sequentially.

20. The method according to claim 17, further comprising pretreating the keratinic fiber prior to contact with the at least one component A and the at least one component B, wherein pretreating the keratinic fiber comprises contacting the keratinic fiber with an agent selected from the group consisting of bleaching agents, oxidation colorants and combinations thereof.

* * * * *